United States Patent [19]

Gross et al.

[11] Patent Number: 5,236,078
[45] Date of Patent: * Aug. 17, 1993

[54] APPARATUS FOR FIXING THE POSITION OF THE TEST ZONES OF A TEST STRIP AND FOR REVERSING THE LATTER

[75] Inventors: Jüurgen Gross, Hofheim am Taunus; Rüdiger Sominek; Hans D. Sanger, both of Frankfurt am Main, all of Fed. Rep. of Germany

[73] Assignee: Hoechst Aktiengesellschaft, Frankfurt am Main, Fed. Rep. of Germany

[ * ] Notice: The portion of the term of this patent subsequent to Nov. 27, 2007 has been disclaimed.

[21] Appl. No.: 785,219

[22] Filed: Oct. 28, 1991

Related U.S. Application Data

[60] Continuation of Ser. No. 571,102, Aug. 23, 1990, abandoned, which is a division of Ser. No. 78,662, Jul. 28, 1987, Pat. No. 4,972,935.

[30] Foreign Application Priority Data

Jul. 30, 1986 [DE] Fed. Rep. of Germany ....... 3625704

[51] Int. Cl.⁵ ............................................. B65G 47/24
[52] U.S. Cl. ..................................... 198/395; 198/399
[58] Field of Search ............................... 198/395, 399

[56] References Cited

U.S. PATENT DOCUMENTS 2,759,589  8/1956  Hall et al. .......................... 198/399
4,777,907 10/1988  Sanger et al. ...................... 198/399

Primary Examiner—Joseph E. Valenza
Attorney, Agent, or Firm—Finnegan, Henderson, Farabow, Garrett & Dunner

[57] ABSTRACT

In the apparatus for fixing the position of the test zones of a test strip and for reversing the latter, a guide (8) opens into a reversing device (1,1a) for the test strips (2). Between the guide and the reversing device is arranged a closing means (9) for the guide, which is connected to a holding device (10) via a lever (5). The holding device (10) projects into the guide and is mounted rotatably in synchronism with the closing means (9). It is also equipped with a drive device (7). The reversing device has a moveable stop (4, 4a) which is driven by a position-detection means (3) arranged in the guide (8).

2 Claims, 1 Drawing Sheet

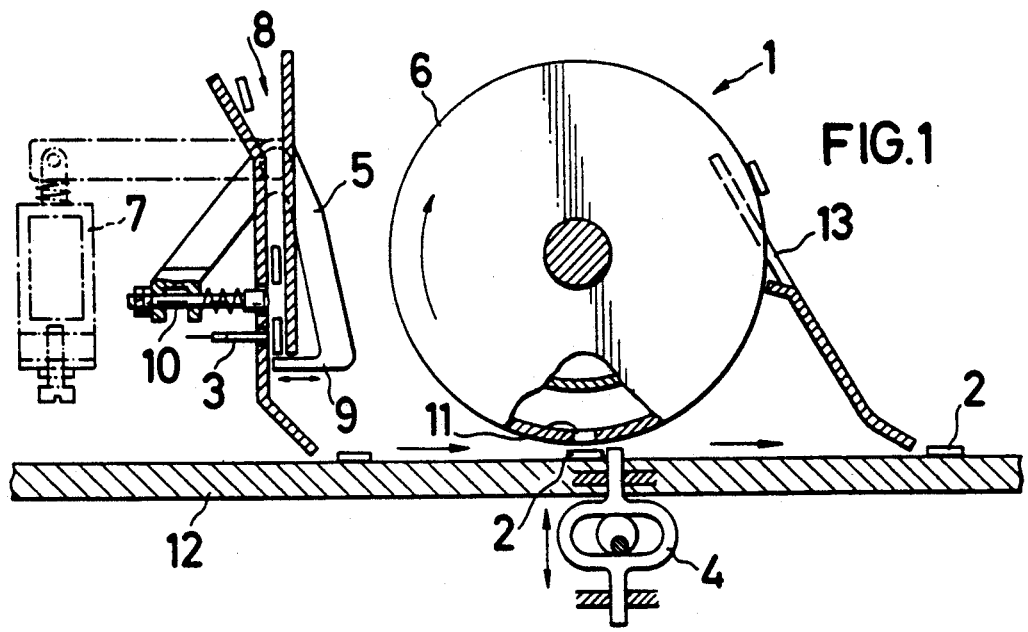
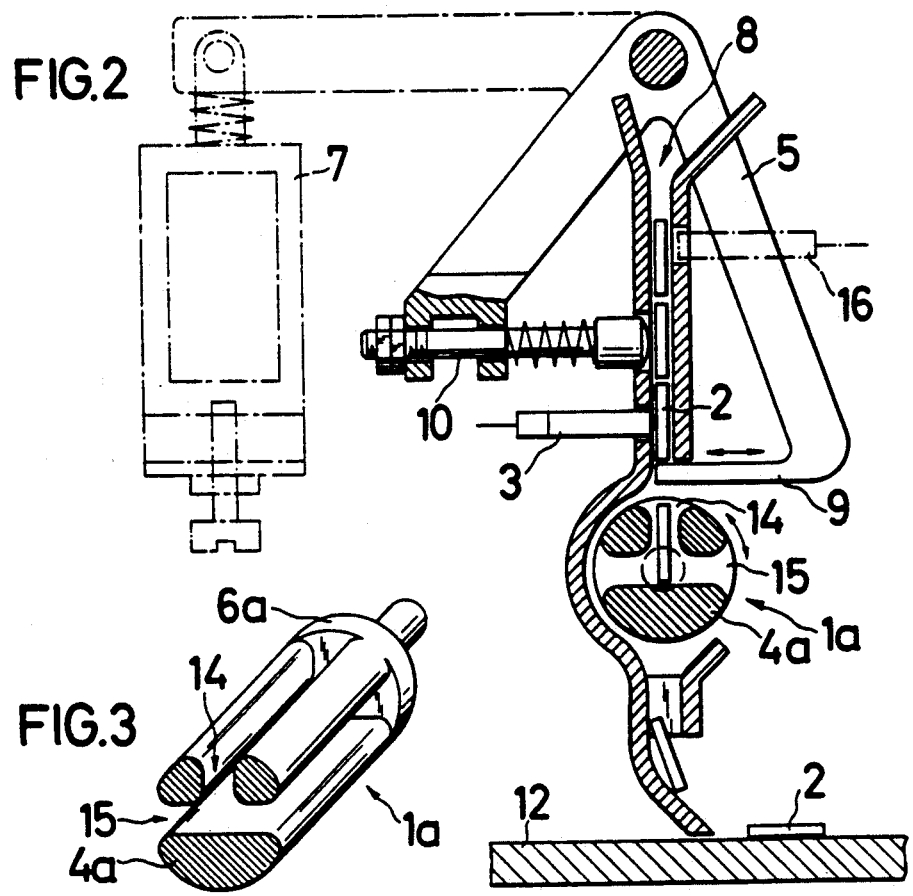

APPARATUS FOR FIXING THE POSITION OF THE TEST ZONES OF A TEST STRIP AND FOR REVERSING THE LATTER

This application is a continuation of application Ser. No. 07/571,102, filed Aug. 23, 1990 now abandoned; which is a divisional of application Ser. No. 07/078,662, filed Jul. 28, 1987, now U.S. Pat. No. 4,972,935.

DESCRIPTION

The invention relates to an apparatus for fixing the position of the test zones of a test strip and for reversing the latter, such test strips being used, for example, for medical tests, especially for analyzing urine. It is part of a line serving for the automatic feeding, sorting, moistening and insertion of test strips in an analyzer, for example a multi-channel photometer.

For generally known urine diagnostics, so-called multiple test strips for determining bilirubin, urobilinogen, ketone bodies, ascorbic acid, glucose, protein, nitrite, pH and blood are available. Test strips of this type contain several test zones, on which the reagents belonging to the particular test are arranged as indicators. The test strips are moistened with urine by hand and are subsequently introduced into the analyzer. This work is to be automated. Among other things, an apparatus for fixing the position of the test zones and, if appropriate, reversing the test strips, so that the test zones of all the strips face upwards, is necessary for this purpose.

The invention achieves the object by a guide opening into a reversing device for the test strips, there being arranged between the guide and reversing device a closing means for the guide, the said closing means being connected via a lever to a holding device for the test strips which projects into the guide, is mounted rotatably in synchronism with the closing means and is equipped with a drive device, and the reversing device having a moveable stop which is driven by a position-detection means arranged in the guide and which causes the test strips.

The reversing device can comprise an evacuable rotatably mounted hollow roller which is arranged at a distance above a transport device for the test strips and with this forms a gap and which, on its peripheral surface, has a leakage orifice, via which the test strip is sucked up and taken up by the roller when the stop, arranged in the gap between the roller and transport device, has stopped the test strip. However, the reversing device can also comprise a roller which has a T-shaped slot parallel to its axis of rotation, and the part of the roller located opposite the crosspiece of the T-contour is designed as a stop. A monitoring device for the test-strip supply can be arranged in the guide.

The invention is explained in detail below with reference to drawings which illustrate only one possible embodiment. FIG. 1 shows a side view of the apparatus in section, FIG. 2 shows an alternative form of the apparatus, likewise in a side view and in section, and FIG. 3 shows the roller according to FIG. 2 in an isometric representation, partially in section.

The apparatus has a guide (8) which opens into a reversing device (1), (1a) for the test strips (2). Between the guide (8) and the reversing device (1), (1a) is arranged a closing means (9) for the guide. The closing means (9) is connected via a lever (5) to a holding device (10), for example a spring-loaded plunger for the test strips (2). The holding device (10) projects into the guide (8) and is mounted rotatably in synchronism with the closing means. When the closing means (9) allows the test strip to pass out of the guide (8), the following test strip is retained in the guide by the holding device (10), until the guide is closed again. The holding device and closing means are equipped with a drive device (7). The reversing device (1), (1a) has a moveable stop (4) (4a) which is driven by means of the prepared pulses from a position-detection means (3), for example, a reflex-light barrier. The position of the test zone on the test strip is fixed by the position detection means (3). If it points in the wrong direction, the stop prevents the test strip from being transported further to the analyzer (not shown). The test strip is reversed. Reversal can be carried out, according to FIG. 1, by means of a hollow roller (6) which is evacuable and which has a leakage orifice (11). When the test strip is stopped by the stop (4), it is sucked up by the vacuum via the leakage orifice, held on the roller periphery and reversed in the direction of the arrow as a result of the rotation of the roller. The test strip is taken off the roller by means of the stripper (13).

According to FIG. 2, reversal is carried out by means of a roller (6a) which is provided with a slot of T-shaped cross-section parallel to its axis of rotation. The orifice (15) is intended as a passage orifice in the roller (6a), whilst the crosspiece (14) of the T-contour ends at the stop (4a). When the position-detection means (3) signals the correct position of the test strip, the test strip can pass through the roller (6a) without obstruction. Otherwise, it is stopped by the stop (4a) and reversed through 180° as a result of the rotation of the roller (6a). In order to monitor the test-strip supply in the guide, the latter can be equipped with a monitoring device (16).

We claim:

1. An apparatus for reversing the orientation of a test strip relative to a conveying surface, comprising:
   a conveying surface for receiving and conveying the test strip;
   means for guiding the test strip onto said conveying surface;
   position-detection means for detecting the orientation of said test strip; and
   means, acting in cooperation with said guiding means and said position-detection means, for selectively reversing the orientation of said test strip relative to said conveying surface, said reversing means including a roller rotatable about an axis of rotation, said roller having a slot disposed substantially parallel to said axis of rotation, said slot being configured such that in a first position of said roller the test strip is received therein and its orientation reversed by rotation of said roller, and such that in a second position of said roller, the test strip passes through said roller without change in its orientation.

2. The apparatus of claim 1, wherein said slot is substantially T-shaped to provide a diametric through-passage and a radial blocked passage, said radial blocked passage receiving said test strip in said first position and said diametric through-passage receiving said test strip in said second position.

* * * * *

UNITED STATES PATENT AND TRADEMARK OFFICE
CERTIFICATE OF CORRECTION

PATENT NO. : 5,236,078
DATED : August 17, 1993
INVENTOR(S) : Gross et al.

It is certified that error appears in the above-identified patent and that said Letters Patent is hereby corrected as shown below:

On title page, item [75] Inventors: change "Jüurgen" to --Jürgen--.

Signed and Sealed this

Third Day of May, 1994

Attest:

BRUCE LEHMAN

Attesting Officer     Commissioner of Patents and Trademarks